US008357817B2

(12) United States Patent
Barboiu et al.

(10) Patent No.: US 8,357,817 B2
(45) Date of Patent: Jan. 22, 2013

(54) SULFONE HYBRID PRECURSOR, METHOD OF SYNTHESIZING SAME, AND USES THEREOF

(75) Inventors: Mihail-Dumitru Barboiu, Montpellier (FR); Mathieu Michau, Ponteilla (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 12/933,593

(22) PCT Filed: Mar. 19, 2009

(86) PCT No.: PCT/FR2009/000288
§ 371 (c)(1),
(2), (4) Date: Apr. 20, 2011

(87) PCT Pub. No.: WO2009/122043
PCT Pub. Date: Oct. 8, 2009

(65) Prior Publication Data
US 2011/0190526 A1    Aug. 4, 2011

(30) Foreign Application Priority Data
Mar. 19, 2008  (FR) ...................... 08 01508

(51) Int. Cl.
*C07F 7/10* (2006.01)
(52) U.S. Cl. .................. 556/421; 556/413; 556/420
(58) Field of Classification Search .................. 556/421; 521/27, 25; 429/429
See application file for complete search history.

(56) References Cited

U.S. PATENT DOCUMENTS

| 6,492,481 B1 | 12/2002 | Davis et al. |
| 2004/0003473 A1 | 1/2004 | Glenn et al. |
| 2005/0164063 A1* | 7/2005 | Wariishi et al. ................. 429/33 |

FOREIGN PATENT DOCUMENTS

| EP | 1142933 | 10/2001 |
| WO | WO 2005/111114 A1 * | 11/2005 |

OTHER PUBLICATIONS

Jeong et al; Molecular crystals and liquid crystals, vol. 425, p. 173-180, 2004.*
Sung et al., "Novel Thermally Stable Cross-Linked Nonlinear Optical Silica Films Prepared by a Sol-Gel Process," *Chem. Mater.*, 1998, pp. 1642-1646, vol. 10.
Lindner, et al., "Supported Organometallic Complexes Part XXX. Hydroformylation of 1-hexene in interphases—the Influence of Different Kinds of Inorganic-Organic hybrid Co-Condensation Agents on the Catalytic Activity," *Journal of Organometallic Chemistry*, 2002, pp. 165-172, vol. 641.

* cited by examiner

*Primary Examiner* — Johann Richter
*Assistant Examiner* — Pancham Bakshi
(74) *Attorney, Agent, or Firm* — Womble Carlyle Sandridge & Rice, LLP

(57) ABSTRACT

The present invention relates to a novel sulfone hybrid precursor, to the synthesis method thereof, and to the uses thereof, particularly for preparing proton-exchanging electrolyte membranes as the functional hybrid charge in a host structure; for the manufacture of functional hybrid nanoparticles by sol-gel polymerization; for the use as a fluidifying agent; for the production of surface coverings through chemical grafting by means of sol-gel polymerization; for the use as a hygroscopic agent; and for the use as a bonding or structuring agent.

22 Claims, 7 Drawing Sheets

SULFONE HYBRID PRECURSOR, METHOD OF SYNTHESIZING SAME, AND USES THEREOF

FIELD OF THE INVENTION

The present invention relates to a novel sulfonated hybrid precursor, to a process for synthesizing it and to its uses, especially for the preparation of proton-exchange electrolyte membranes, as a functional hybrid filler in a host structure after in situ sol-gel polymerization, for the manufacture by sol-gel polymerization of functional hybrid nanoparticles, as a thinning agent (for example for reducing the viscosity of concentrated pastes such as ceramics and slips), for producing surface coatings by chemical grafting via sol-gel polymerization (formation of a grafted monolayer that increases the surface hydrophilicity), as a hygroscopic agent, as a binder or as a structuring agent.

The invention that will be described hereinbelow falls especially within the context of energy production and management. Nowadays, the production and consumption of energy are predominantly based on the combustion of fossil resources, which is predicted to have in the long term a major impact on the worldwide economy and an unfavorable effect on the environment and the ecology of the planet (shortages of fossil fuels and increasing atmospheric pollution). This is why the electrochemical conversion of energy using fuel cells is seriously considered as a source of alternative energy and power (energy vector).

BACKGROUND

Proton-exchange membrane fuel cells, also known as polymer electrolyte membrane fuel cells (or PEMFC) are a type of fuel cell developed for applications in transportation and also for portable applications. The principle of fuel cells was demonstrated experimentally in 1839 by the British electrochemist Sir William Grove. The first fuel cells of PEMFC type were developed in the United States in the 1960s by General Electric for space applications. Currently, this type of cell, which is designed to function at intermediate temperatures (40-120° C.), is developed internationally by the motor vehicle and portable electronics industries. However, despite undeniable environmental advantages, and superior energy yields, fuel cells are only just beginning to compete with internal combustion engines on account of the costs that are still high (raw materials, service lives).

The core of a fuel cell of PEMFC type is composed of a polymer electrolyte membrane, electrodes (anode and cathode, usually in the form of thin layers of platinum) and bipolar plates serving for gas diffusion.

Fuel cells functioning with proton-exchange polymer electrolyte membranes allow the conversion of the chemical energy of gases ($H_2/O_2$) into electrical energy with high energy yields and with no discharge of pollutant, according to the following equations:

Reaction at the cathode (site of oxygen reduction):

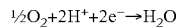

Reaction at the anode (site of hydrogen oxidation):

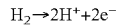

Since the two electrodes are separated by the electrolyte (membrane), the fuel to be oxidized (hydrogen) is conveyed to the anode, and the cathode is fed with oxygen (or more simply with air, optionally enriched with oxygen). At the anode, the dihydrogen reacts and releases two electrons (oxidation) that feed an external electrical circuit connecting the anode and the cathode. At the cathode, the cathodic reduction of the oxygen takes place. The reagents are, in principle, introduced continuously into the device and the electromotive force of the cell is equal to the difference of the electrode potentials. A universally known overall reaction is thus obtained:

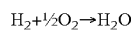

Water is thus produced by the normal functioning of the cell, which must be evacuated outside the membrane. Management of the water is crucial for the performance of the cell; care should be taken to ensure that the amount of water remains constantly at an optimum level, ensuring correct functioning of the cell. In particular, an excess of water leads to excessive swelling of the membrane, to congestion of the distribution channels or electrodes and to a negative effect on the access of the gases to the catalytic sites, whereas an insufficient amount of water leads to dryness of the membrane, which is harmful to its conductivity and to the yield of the cell.

The role of the membrane is thus to ensure the transportation of protons ($H^+$) from the anode to the cathode and thus to allow the electrochemical reaction. However, it should not conduct electrons, which would create a short circuit in the fuel cell. The membrane should be resistant to the reductive environment at the anode and, at the same time, to an oxidative environment at the cathode, and should also prevent the mixing of the hydrogen contained at the anode with the oxygen contained at the cathode.

One of the first proton-transporting polymers that was used for producing such membranes, and which today remains the reference in this field, is Nafion®, a perfluorosulfonic polymer developed and perfected in 1968 by the American company Du Pont de Nemours. Historically, the NASA Gemini space programs of the 1960s used fuel cells comprising membranes of sulfonated polystyrene type, but these were very quickly supplanted by Nafion® membranes, which made it possible to improve the performance of PEMFCs. In chemical terms, it is an organic polymer, formed from a flexible fluorocarbon chain on which are randomly distributed ionic groups (Mauritz K. A. et al., *Chem Rev.*, 2004, 104, 4535-4585). On the principle of Nafion®, other perfluorosulfonic commercial polymers exist, such as those sold under the trade names Aciplex® (Asahi Chemical Company, Japan) or Flemion® (Asahi Glass Company, Japan).

The membranes manufactured from these polymers are by nature very chemically, thermally and mechanically stable (flexibility). They have good electrochemical properties with high conductivity, of the order of 0.1 S·cm$^{-1}$ at room temperature and at 100% relative humidity (according to the manufacturer's data for Nafion®). However, these membranes must operate at a temperature below 90° C. and must always remain saturated with water to allow efficient movement of the $H^+$ ions. Specifically, the production of protons takes place mainly via a mechanism of Grotthus type, i.e. via the jumping of protons along the ionic and hydrophilic conduction pathways (Mauritz K. A. et al., 2004, mentioned above). Moreover, the synthesis of these membranes is long, difficult, or even dangerous taking into account the use of fluorine, which partly justifies their very high cost price. Furthermore, they are not entirely satisfactory as regards the problems associated with water management and temperature changes. Specifically, when the system undergoes numerous variations in the level of humidity, the appearance of successive cycles of swelling and restructuring of the membrane is noted, leading to substantial fatigue. Moreover, Nafion® is a polymer that quite naturally undergoes a glass transition (Tg=120° C.), which contributes toward its accelerated aging and to the appearance of structural reorganizations and mechanical weaknesses (failures), thus limiting its service life.

Other alternative types of polymers that may be used for the preparation of electrolyte membranes have also already been proposed. These are in particular sulfonated or doped thermostable polymers (sulfonated polyaryl ether ketones, polybenzimidazoles, polyaryl ether sulfones, etc.). These polymers lead to membranes that also have certain drawbacks, especially in terms of conductivity (performance), service life and water management.

Patent application US 2005/0 164 063 describes the synthesis of various solid compounds and electrolytes obtained from silsesquioxane-based precursors in which a siloxane function is attached to a phenylsulfonate group via a divalent group free of urea functions. Such structures, in which the divalent group linking the siloxane function to the phenylsulfonate is an alkyl or aryl radical, have the drawback of having poor conductivity (*Electrochimica Acta*, 2003, 48, 2181-2186).

This is why, to overcome the respective weaknesses of each of these systems, many studies for modification by incorporation of inorganic phases have been performed in recent years, and have led to an overall improvement in the properties of PEMFCs. This is reflected in particular in the water management and also in the behavior of the materials at high temperature (dehydration) and their long-term stability. These concepts became generalized with the appearance of hybrid membranes, which also make it possible to demonstrate the importance of the presence of a continuous inorganic network within the conductive electrolyte.

Rhodium-based monomer complexes obtained by reacting (p-aminophenyl)diphenylphosphine with 3-isocyanatopropyltriethoxysilane, with improved catalytic properties, are also known and used for sol-gel polymerizations (*J. Organomet. Chem.*, 2002, 641, 165-172).

Films prepared by reacting an alkoxysilane with 4-[(4"-aminophenyl)sulfonyl]-4'-[N,N'-bis(2-hydroxyethyl)amino] azobenzene via sol-gel polymerization are also described in Chem. Mater., 1998, 10, 1642-1646, for their uses in the field of optics.

Unfortunately, at the present time, no membrane, irrespective of its nature, fully satisfies the rigorous requirements of PEMFC constructors and users. Although many operational technical devices using these electrochemical systems have appeared on the market, for instance the Genepac fuel cell arising from a partnership between PSA Peugeot Citroen and the Commissariat à l'Energie Atomique, and whose power may be up to 80 kW, technological obstacles remain to be overcome.

Firstly, in terms of water management: as has been seen previously, it is of paramount importance to manage the water produced during the functioning of the cell and its influence on the properties of the electrolyte membrane (especially the conductivity). This need to optimally control and manage the water transports taking place in a PEMFC (inlets, outlets, generation, and back-diffusion between cathode and anode) remains a major constraint that encourages the production of electrolytes that are less dependent on the relative humidity.

In terms of operating temperature also: fuel cells of Nafion® type can only work at maximum temperatures of 90° C. For higher temperatures, the membranes can no longer ensure suitable proton conductivity on account of their inability to retain water. Their yield decreases as a function of the drop in relative humidity combined with the increase in temperature. Now, the application of fuel cells to transportation vehicles requires the use of membranes that can function satisfactorily at temperatures above 90° C., in particular at temperatures between 120 and 150° C. Membranes of this type do not currently exist on the market.

Finally, in terms of manufacturing cost: to enable the mass development of this technology and the generalization of these power generators destined for a bright future, the problem remains of the cost of manufacture of the electrolyte membrane per se, but also the cost of manufacture of the fuel cell core (AME) associated with the use of platinum as a catalyst.

SUMMARY OF THE INVENTION

The inventors thus set themselves the aim of developing a novel precursor for overcoming these various drawbacks, which can be used especially for the simple and inexpensive preparation of electrolyte hybrid membranes that have improved properties when compared with the existing membranes, in particular in terms of conductivity/performance, water management and operating temperature, and in terms of thermal and chemical stability. This aim is achieved by using the compounds of formula (I) that are defined below and that constitute, in this respect, the first subject of the present invention.

Consequently, the subject of the present invention is the compounds of formula (I) below:

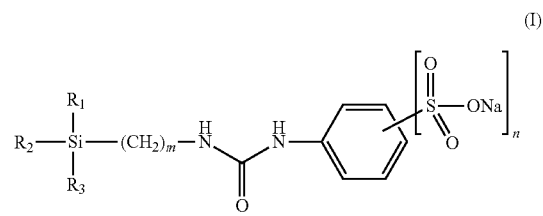

in which:

$R_1$ and $R_3$ are identical and represent a methyloxy or ethyloxy radical;

$R_2$ represents a methyl, ethyl, methyloxy, ethyloxy or phenyl radical;

m is an integer ranging from 2 to 6 inclusive;

n is an integer equal to 1 or 2.

The compounds of formula (I) above in which $R_1$ and $R_3$ represent an ethyloxy radical are particularly preferred.

Among the radicals mentioned above for $R_2$, the ethyloxy radical is particularly preferred.

According to one preferred embodiment of the invention, $R_1 = R_2 = R_3 =$ ethyloxy.

Among the values given for m, the compounds of formula (I) in which m=3 are preferred.

In the compounds of formula (I) above, when n=1, the sodium sulfonate group occupies the para position of the phenyl ring relative to the carbon atom attached to the nitrogen atom of the urea group. When n=2, the two sulfonate groups are either each in the meta position relative to the carbon atom attached to the nitrogen atom of the urea group, or, respectively, in the para and meta position relative to the carbon atom attached to the nitrogen atom of the urea group.

These preferences correspond to configurations (I-1) to (I-3) below:

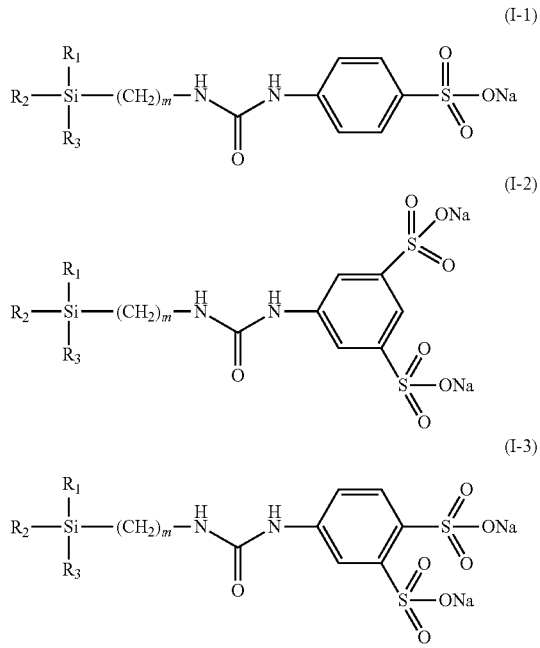

in which $R_1$, $R_2$, $R_3$ and m have the same meanings as those indicated above for the compounds of formula (I).

Among these compounds, the compounds in which n=1, i.e. the compounds of formula (I-1), are preferred.

Among the compounds of formula (I) above, 3-(triethoxysilyl)propyl-3-(4-sodium sulfonate)phenyl)urea is particularly preferred; this compound corresponds to the following formula:

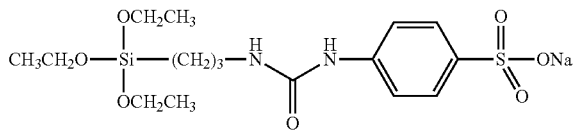

A subject of the present invention is also the process for synthesizing the compounds of formula (I) above. This process is characterized in that it comprises the following steps:

1) totally dehydrating an aminobenzene sulfonate of formula (II) below:

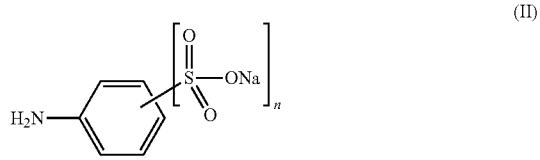

in which n is an integer equal to 1 or 2, to obtain an anhydrous aminobenzene sulfonate of formula (II), 2) dissolving the anhydrous aminobenzene sulfonate of formula (II) obtained above in the preceding step in an anhydrous organic solvent chosen from methanol, dimethylformamide (DMF) and N,N-dimethylacetamide and mixtures thereof; anhydrous methanol being particularly preferred;

3) placing said solution under vacuum and under an inert atmosphere;

4) adding to said solution, in excess and at room temperature, an anhydrous isocyanate compound of formula (III) below:

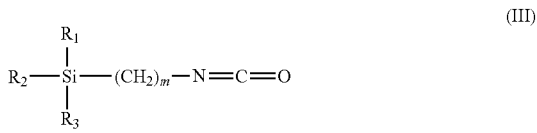

in which:
$R_1$ and $R_3$ are identical and represent a methyloxy or ethyloxy radical;
$R_2$ represents a methyl, ethyl, methyloxy, ethyloxy or phenyl radical;
m is an integer ranging from 2 to 6 inclusive;

5) precipitating the expected compound of formula (I) in an aprotic solvent; and 6) washing said compound of formula (I) in an aprotic solvent.

Step 1) of dehydration of the aminobenzene sulfonate of formula (II) may be performed, for example, according to the following protocol: three successive cycles at 150° C. on a drying balance, and 1 hour in a bell jar under vacuum at 60° C.

During step 4), the isocyanate compound of formula (III) is preferably used in an excess representing from 1.2 to 1.3 equivalents relative to the amount of aminobenzene sulfonate of formula (II) used.

According to one preferred embodiment of the invention, after step 4), the solution containing the aminobenzene sulfonate of formula (II) and the isocyanate compound of formula (III) is maintained at a temperature of between 60 and 80° C. inclusive, for a time preferably ranging from 3 to 12 hours approximately, so as to increase the reaction yield.

The aprotic solvent used during steps 5) and 6) is preferably chosen from acetonitrile, ether and acetone, and mixtures thereof. In this respect, the use of an acetonitrile/ether mixture (50/50: v/v) is particularly advantageous.

After the washing step, the compound of formula (I) thus obtained may be dried and stored in a desiccator, according to standard methods (glove box under an inert atmosphere, $P_2O_5$ desiccant, silica gel, etc.).

The compounds of formula (I) described above may advantageously be used for the preparation of electrolyte polymer membranes.

Another subject of the present invention is thus the use of at least one compound of formula (I) as defined above for the preparation of a proton-conducting polymer electrolyte membrane.

According to one preferred embodiment of the invention, the use of 3-(triethoxysilyl)propyl-3-(4-sodium sulfonate) phenyl)urea is, in this case, particularly advantageous.

The process for preparing these electrolyte membranes may be performed conventionally according to a sol-gel polymerization process with nucleophilic catalysis using a nucleophilic catalyst.

It generally comprises the following steps:
1) dissolving at least one compound of formula (I) in an anhydrous solvent (which may be chosen, for example, from methanol, DMF and dimethylacetamide), 2) polymerizing said compound of formula (I) by adding a nucleophilic catalyst chosen from primary amines and imidazole derivatives, in the presence of water to obtain a gel,
3) forming said gel,
4) drying said gel to obtain a solid material in the form of a polymeric film,
5) Na$^+$/H$^+$ ionic exchange by immersing said polymeric film in an acidic solution, and
6) rinsing said polymeric film with water to remove all trace of acid.

According to one preferred embodiment of this process, a plasticizing precursor may be added to the solution of the compound(s) of formula (I) before initiating the polymerization reaction, preferably with vigorous stirring.

The presence of such a plasticizing precursor makes it possible to increase the hydrophobicity, the flexibility and the elasticity of the electrolyte membrane.

When it is used, the plasticizing precursor is preferably chosen from the compounds of formula (IV) below:

Step 2) is preferably performed at room temperature.

According to one preferred embodiment of this process, the forming of the membranes in step 3) is performed such that their thickness is between 100 and 200 μm approximately. This makes it possible, when the polymer membrane is then used as electrolyte in a fuel cell, to increase the performance of the system during functioning (lower intrinsic resistance).

If so desired, after step 4), the membrane may be dried and stored in a desiccator. In this case, the membrane will have to be gradually rehydrated, for example by successive immersions in an aqueous-alcoholic medium, for instance an ethanol/water mixture, before undergoing the ion-exchange step 5) and the rinsing step 6) that are necessary for its activation and thus its use.

The ion exchange of step 5) is preferably performed by immersing the membrane in a hydrochloric acid solution with a molarity between 1 and 4 M inclusive.

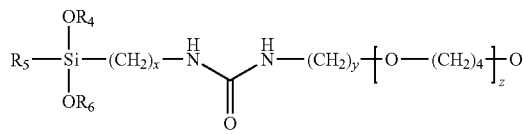 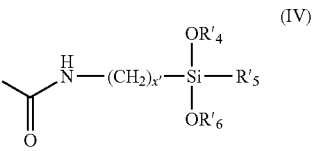

(IV)

in which:
$R_4$, $R'_4$, $R_6$ and $R'_6$ are identical and represent a methyl or ethyl radical;
$R_5$ and $R'_5$, which may be identical or different, represent a methyl, ethyl, methyloxy, ethyloxy or phenyl radical;
x and x', and y and y', which may be identical or different, are integers ranging from 2 to 6 inclusive;
z is an integer ranging from 8 to 16 inclusive.

Among the radicals mentioned above for $R_4$, $R'_4$, $R_6$ and $R'_6$, the ethyl radical is particularly preferred.

Among the radicals mentioned above for $R_5$ and $R'_5$, the ethyloxy radical is particularly preferred.

According to one preferred embodiment of the invention, $R_4=R'_4=R_6=R'_6=$ethyl.

Among the values given for x, x', y and y', the preferred compounds are those of formula (IV) in which x=x'=y=y'=3.
z is preferably an integer ranging from 12 to 14 inclusive; the value z=13 being the most particularly preferred.

According to one most particularly preferred embodiment, the compounds of formula (IV) are chosen from molecules that are symmetrical relative to the polytetrahydrofuran unit.

A compound of formula (IV) above that may be mentioned in particular is bis(3-(triethoxysilyl)propylurea)-3-poly(tetrahydrofuran) in which the number (z) of tetrahydrofuran units=13.

When a plasticizing precursor of formula (IV) is used, it preferably represents from 10 to 40 mol % approximately and more particularly from 15 to 25 mol % approximately relative to the number of moles of compound of formula (I).

Among the nucleophilic catalysts that may be used in step 2) of the process, benzylamine (primary amine) is particularly preferred.

The amount of catalyst used preferably ranges from 2 to 3 equivalents relative to the total number of silicons present in the reaction medium, the amount of water itself being between 4 and 6 equivalents relative to the total number of silicon.

The membranes obtained using at least one compound of formula (I) in accordance with the invention according to the process that has just been described above have the following advantages:
they are easy to prepare via an inexpensive synthetic process. They can easily be produced in large amount without any heavy equipment, and do not require any particular safety conditions. Moreover, many possibilities exist for forming the gel: casting (tape-casting, spin-coating), hot pressing, extrusion, etc. Moreover, the synthetic strategy via supramolecular self-assembly and sol-gel polymerization via nucleophilic catalysis leads to the production of highly organized and crystalline membrane films,
they have excellent conductivity properties, 4 to 8 times higher than those of the Nafion®-based reference membrane that usually constitutes the membranes conventionally used in the manufacture of fuel cell cores. This consequently makes them a material of choice for use as a proton-conducting electrolyte polymer membrane in fuel cells of PEMFC type,
they also have noteworthy homogeneity and chemical and thermal stability properties due to controlled nanostructuring during their synthesis and to the continuous presence of an inorganic silica backbone/matrix (Si—O—Si). The degradation temperatures of these membranes are above 330° C. and they also have good stability in a hydrolytic and/or oxidative environment.

The membranes in accordance with the invention have fine architecture in the form of hydrophilic ionic channels of nanometric dimensions within an inorganic silica matrix. This particular architecture of the membranes in accordance with the invention is favorable to retaining water, but also to proton transport. This may be an advantage in terms of water management by thus increasing their water retention capacity at high temperature (slower drying than other electrolytes).

Finally, the compounds of formula (I) in accordance with the present invention may also be used:

as functional hybrid filler in a host structure after in situ sol-gel polymerization (since they thus lead to a conductive organo-mineral particle). There is thus a great difference with a basic mineral filler, in the form of non-functional oxide nanoparticles ($SiO_2$, $TiO_2$, $ZrO_2$, for example), which are conventionally used for improving just the mechanical or physical properties). Mention may be made, for example, of incorporation into organic polymer membranes or ion-exchange resins (increase in conductivity, exchange capacity and mechanical stability since, after in situ sol-gel polymerization, nanoparticles with an inorganic core ($SiO_2$) will be obtained), for the manufacture by sol-gel polymerization of functional hybrid nanoparticles ($SiO_2$ inorganic core and hydrophilic organic surface), as a thinning agent (for example for reducing the viscosity of concentrated pastes such as ceramics or slips). This may especially make it possible to improve the flow in aqueous media for concentrated solutions, for the production of surface coatings by chemical grafting via sol-gel polymerization (hybrid polymer films). Grafted monolayers that increase the surface hydrophilicity are thus obtained. The surfaces concerned by such a coating are, for example, silicon wafers and oxide surfaces, as hygroscopic agent (water adsorption and retention), as formulation binder (ambivalence of the organic/inorganic functions), as structuring agent (imprint/template) for inducing a lamellar structure in other materials (preferentially silica compounds) by transferring the self-organization intrinsic to the compounds of formula (I) in accordance with the invention (supramolecular self-assembly by hydrogen interaction and regrouping of the $SO_3$-functions).

The industries concerned by such applications belong to many sectors of activity, among which mention may be made especially of the glass, thin layer, metal oxide, etc. sectors.

DESCRIPTION OF THE FIGURES

Besides the preceding arrangements, the invention also comprises other arrangements that will emerge from the description that follows, which refers to an example of preparation of a compound of formula (I) in accordance with the invention, to an example of preparation of an electrolyte polymer membrane based on a compound of formula (I), and also to the attached FIGS. 1 to 8 in which:

FIG. 4B: magnification ×240 000) showing the submicron organization of the precursor (1) at nanometric scales;

Figure 13:
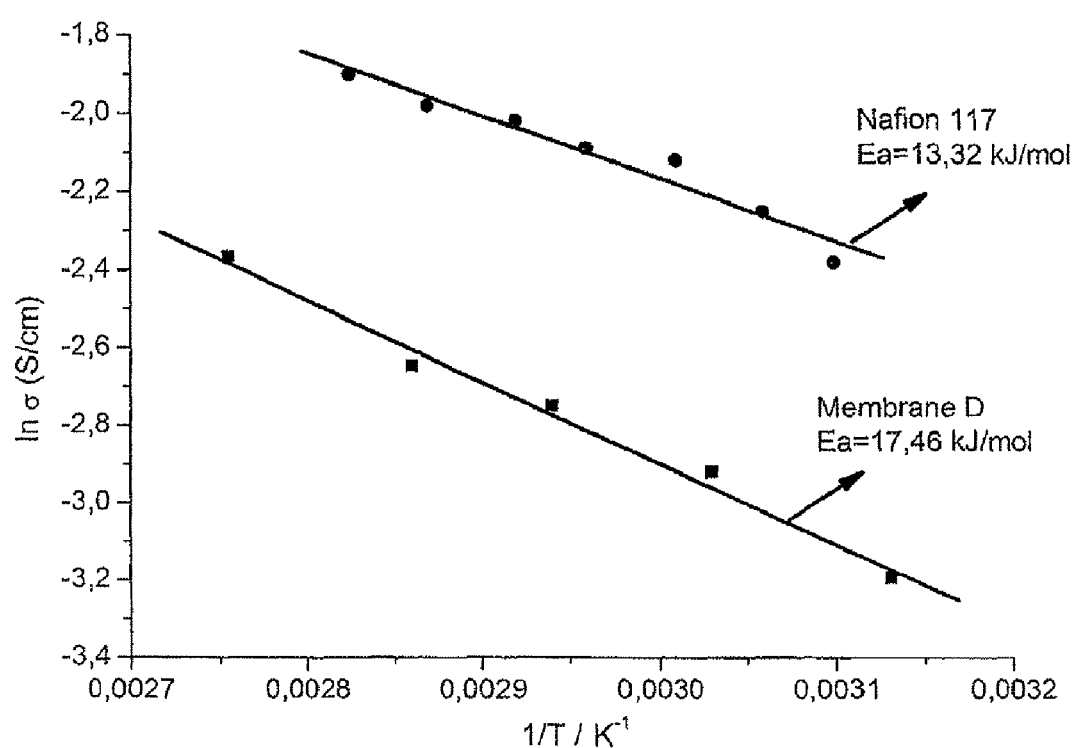

a) cross section of a hybrid membrane according to the invention, b) schematic assembly of the lamellar nanodomains, c) formation of proton-conduction channel bonds comprising the conductive groups —$SO_3H$—$H_2O$;

FIG. 13 shows the Arrhenius curve of the immersed membranes measured by electrochemical impedance spectrometry.

It should be understood, however, that these examples are given merely as illustrations of the invention, of which they do not in any way constitute a limitation.

DETAILED DESCRIPTION OF THE INVENTION

Example 1

Preparation of 3-(Triethoxysilyl)Propyl)-3-(4-Sodium Sulfonate)Phenyl)Urea (Compound (1))

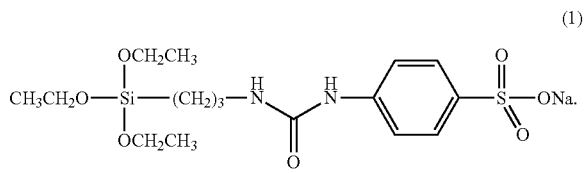

In a first stage, commercial sodium 4-aminobenzenesulfonate dihydrate (2) was dehydrated according to the following protocol: three successive cycles at 150° C. on a drying balance and then 1 hour in a bell jar under vacuum at 60° C. in which the dehydrated product was stored until the time of use. Next, 1 g of sodium 4-aminobenzenesulfonate thus dehydrated (6.67 mmol; 1 eq.) was introduced into a round-bottomed flask containing 30 ml of anhydrous methanol. The solution was stirred, sonicated and placed under vacuum and then under an inert atmosphere ($N_2$). 1.65 g of anhydrous 3-triethoxysilylpropyl isocyanate (5.13 mmol; 1.3 eq.) were then added dropwise to this solution with continuous stirring, and the whole was then refluxed at a temperature of 80° C. for 5 hours. At the end of the reaction, the colorless solution obtained was concentrated under vacuum and then subjected to precipitation and crystallization by slow cooling to a temperature of 4° C. in an acetonitrile/ether mixture (50/50: v/v). The mixture was then filtered very quickly, washed several times with acetonitrile/toluene mixtures (75/25: v/v) to give a white paste, which was immediately dried at 60° C. in a bell jar under vacuum and then stored in a desiccator. This example made it possible to obtain pure compound (1) in a yield of greater than 90% in the form of a hygroscopic white powder.

$^1$H NMR (300 MHz, DMSO): δ (ppm)=0.55 (t, J=8.1 Hz, 2H); 1.14 (t, J=6.3 Hz, 9H); 1.47 (m, J=8.35 Hz, 2H); 3.04 (q, J=7.5 Hz, 2H); 3.74 (q, J=8.1 Hz, 6H); 6.36 (t, J=5.4 Hz, 1H); 7.34 (d, J=6.2 Hz, 2H); 7.46 (d, J=6.4 Hz, 2H); 8.61 (s, 1H).

$^{13}$C NMR (75 MHz, $CDCl_3$): δ (ppm)=7.4; 18.3; 23.5; 39.6; 57.5; 116.2; 126.5; 140.1; 141.5; 153.8.

A structural analysis by X-ray powder diffraction of compound (1) thus obtained was performed using a Philips diffractometer, PanAnalytical X'pert Pro I model, (measurements in Bragg-Brentano mode, graphite secondary monochromator, X'celerator detector, Cu radiation). The diffractogram obtained is shown in the attached FIG. 1, in which the intensity (in arbitrary units) is a function of the diffraction angle (2θ). The crystallographic structure of compound (1) is shown in the attached FIG. 2.

These results demonstrate high crystallinity of this compound. These results show that compound (1) crystallizes in a monoclinic lattice, space group P2 1/c, with a mean volume of 2194.79 Å$^3$ and the following lattice parameters: α=γ=90°; β=116.4°; a=19.499 Å; b=5.014 Å and c=22.449 Å.

Figure 1:
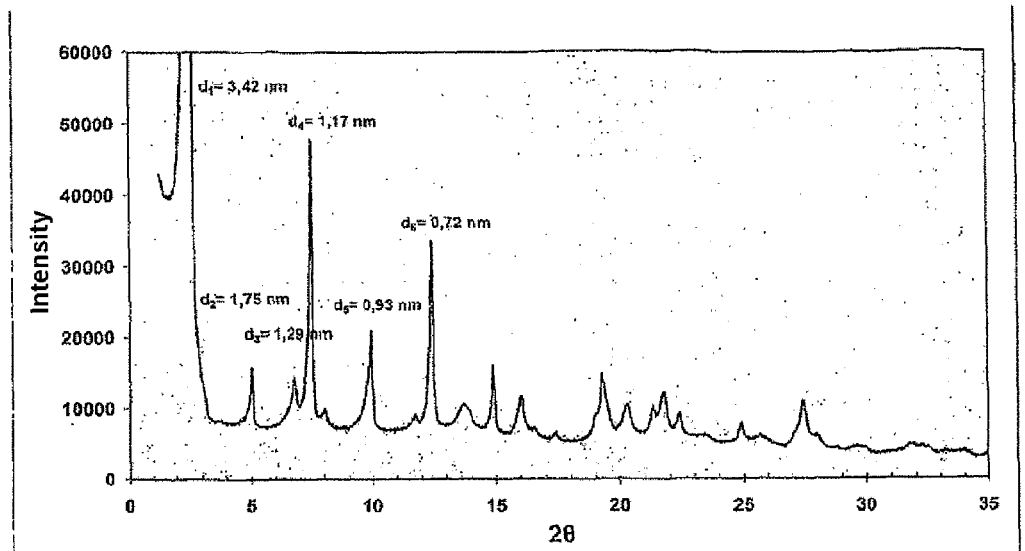
FIG. 1 is the X-ray powder diffractogram of 3-(triethoxysilyl)propyl)-3-(4-sodium sulfonate)phenyl)urea (1) (intensity in arbitrary units as a function of the diffraction angle (2θ))
Figure 2:
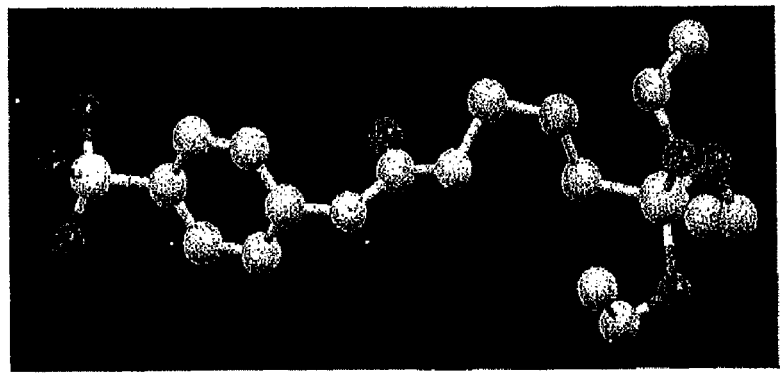
FIG. 2 is the crystallographic structure of compound (1)
Figure 3:
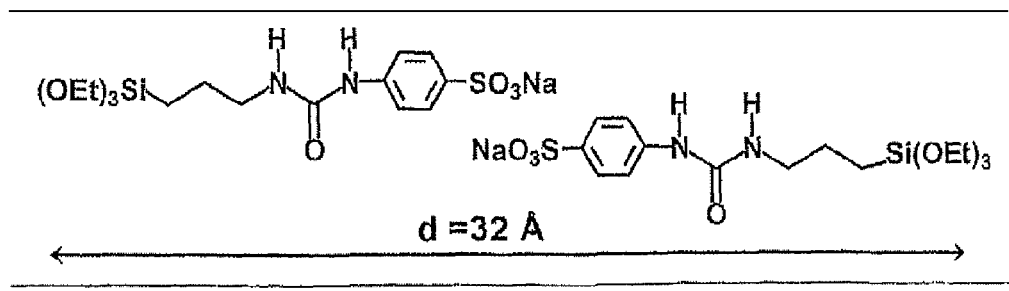
FIG. 3 is a schematic representation of the molecular organization of compound (1) in dimeric form $(1)_2$.

The diffractogram of compound (1) as shown in FIG. 1 has a very strong peak at small angles, corresponding to an interplane distance of 3.42 nm and certainly to the formation of dimers $(1)_2$ at the molecular level, as is shown schematically in the attached FIG. 3. Specifically, it may be considered that this distance corresponds to the face-to-face arrangement of two neighboring molecules, the sulfonate functions of which are close together. Furthermore, the self-assembly via hydrogen bonding of the urea groups makes it possible to obtain a parallel arrangement of the molecular structure of the precursors (1) (oriented isotopic superstructures).

Figure 4:
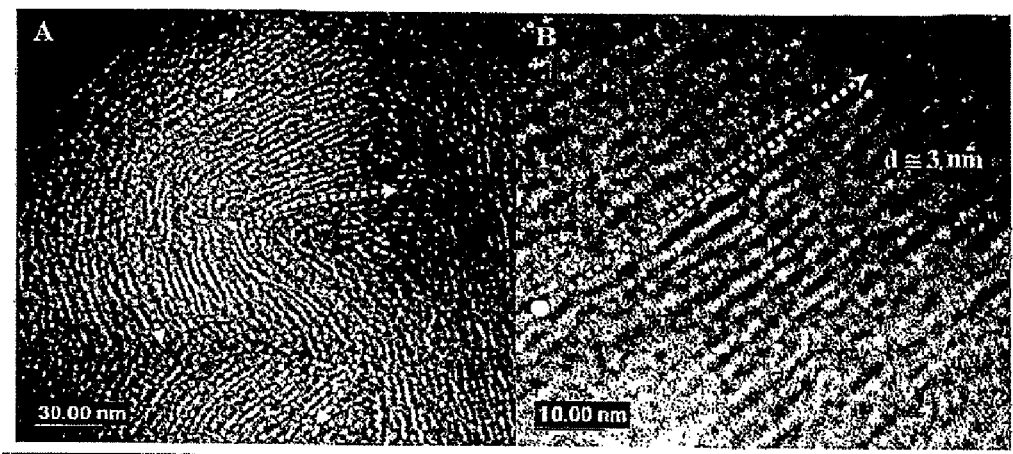
FIG. 4 is a transmission electron microscopy photograph (FIG. 4A: magnification ×80 000.

Transmission electron microscopy analyses revealed very high organization at the submicron level (see the attached FIG. 4). Specifically, these images on the organization of compound (1) at nanometric scales (FIGS. 4A and 4B) demonstrate the formation of continuous molecular channels arranged parallel to each other.

Example 2

Preparation of Hybrid Electrolyte Membranes Based on 3-(Triethoxysilyl)Propyl)-3-(4-Sodium Sulfonate)Phenyl)Urea and on a Plasticizing Hybrid Precursor 1) First step: Synthesis of a plasticizing hybrid precursor: bis(3-(triethoxysilyl)propylurea)-3-poly(tetrahydrofuran) (3)

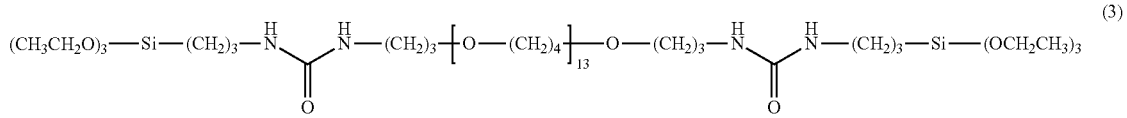

2 g (1 eq.; 1.82 mmol) of poly(tetrahydrofuran)bis(3-aminopropyl) sold by the company Aldrich (reference 436577; $M_n$=1100 i.e. 13 tetrahydrofuran units) were dissolved in 30 ml of an anhydrous chloroform solution. The solution was stirred, sonicated and placed under vacuum and then under an inert atmosphere ($N_2$). 0.94 g (2.1 eq.; 3.8 mmol) of 3-triethoxysilylpropyl isocyanate was then added dropwise to this solution with continuous stirring, and the whole was then refluxed at 80° C. for 20 hours. The reaction mixture was then evaporated under vacuum for 4 hours at a temperature of 80° C. to give a translucent viscous solution. This solution was washed several times with 3×20 ml of an acetonitrile/ether mixture (50/50: v/v) and the expected plasticizing hybrid precursor (3) was recovered in the form of a viscous gel after centrifugation and decantation.

$^1$H NMR (300 MHz, DMSO): δ (ppm)=0.51 (t, J=9.2 Hz); 1.11 (t, J=6.2 Hz); 1.36 (m); 1.50 (m); 1.59 (m); 2.95 (q, J=6.1 Hz); 3.02 (q, J=6.3 Hz); 3.15 (s); 4.42 (s); 3.32 (s); 3.74 (q, J=9.4 Hz); 5.73 (t, J=5.6 Hz); 5.81 (t, J=5.3 Hz).

2) Synthesis of polymer electrolyte membranes

The synthesis of the membranes was performed according to a sol-gel polymerization process with nucleophilic catalysis using benzylamine as catalyst. The reaction medium is formed by compound (1) prepared above in Example 1 as functional hybrid precursor and compound (3) as prepared above in the first step, as plasticizing hybrid precursor.

Compound (1) gives functionality (conduction) to the system and compound (3) allows the physical properties of the material (flexibility) to be adjusted.

To do this, compound (1) was dissolved in 5 ml of an anhydrous methanol solution, followed by dropwise addition of compound (3) with vigorous stirring. The amounts of each of the precursors used to prepare membranes A to G below are presented in Table 1 below:

TABLE 1

| Membrane | Membrane composition | | |
|---|---|---|---|
| | weight % of compound (1) | weight % of compound (3) | mol % of compound (1) |
| A (*) | 0 | 100 | 0 |
| B | 20 | 80 | 47.4 |
| C | 30 | 70 | 60.8 |
| D | 40 | 60 | 64.3 |
| E | 48 | 52 | 70.6 |
| F | 58 | 42 | 78.3 |
| G | 78 | 22 | 84.2 |
| H | 100 | 0 | 100 |

(*): membrane not forming part of the present invention

Each of the solutions was then homogenized by sonication followed by stirring for 30 minutes. 3 eq. of benzylamine (corresponding amount calculated relative to the total number of triethoxysilane groups present in the medium: $nSi(OEt)_3$ total=1 eq.) and water (6 eq.) were then added to initiate the hydrolysis reactions. The whole was stirred vigorously for 45 minutes. The viscosity finally increased gradually to give a viscous gel.

A membrane I containing 35% by weight of compound (1) was also prepared.

3) Forming of the membranes

Each of the gels thus obtained was poured into a circular Teflon® Petri dish, dried at room temperature for 24 hours and then in an oven according to the following heating cycle: 8 hours at 40° C.; 4 hours at 60° C.; 4 hours at 80° C., 2 hours at 100° C. and 1 hour at 120° C. Once dried, the membranes were removed from the molds and then cooled and gradually rehydrated in an ethanol/water mixture (95/5: v/v). $Na^+/H^+$ ion exchange was then performed by dipping the membranes in a 1M hydrochloric acid solution for 24 hours, followed by dipping them for several hours in baths of deionized water (three times for 24 hours) and rinsing them so as to remove any excess acid, until a neutral and constant pH (close to 7) was obtained for the rinsing solution.

4) Results

The electrochemical and thermal properties of membranes A to G thus obtained are shown in Table 2 below, in which those of a reference membrane of Nafion® 117 type 175 μm thick are also mentioned for comparative purposes. The following were thus measured:

1) Ion-exchange capacity (IEC): the IEC is a characteristic measurement, for a given membrane, which defines the ion exchange potential relative to the mass. It thus represents the number of equivalents of ion exchange sites contained in a given amount of membrane. It is generally expressed in milliequivalents of ions per gram (meq./g) of dry membrane in acid form (in this example the counterion is then a proton $H^+$). It was determined for all the membranes via standard acid-base titrations. Experimentally, the electrolyte membrane (ion exchanger) in acid form ($H^+$) was equilibrated in 1 molar sodium chloride (NaCl) solution for 24 hours: a release of protons and replacement with $Na^+$ ions took place. The solution containing the protons could then be assayed with a basic solution of sodium hydroxide (NaOH) type. By using a pH-meter and a suitable colored indicator (for instance phenol red), the equivalence could be determined precisely. The IEC is expressed by the following equation:

$$IEC(\text{meq.}/g) = 1000 \times \frac{C_{NaOH} \times V_{eq}}{M}$$

in which $C_{NaOH}$ is the concentration of the sodium hydroxide basic solution (in mol/L), V (in L) represents the volume of sodium hydroxide required to reach equivalence and M represents the mass (in grams) of the dry membrane.

This finally made it possible to characterize the accessibility of the ion exchange sites and also their real number (relative to a theoretical value).

2) Degree of swelling of the membrane (electrolyte material): this is expressed as a percentage and corresponds to a volume expansion when it is equilibrated in an aqueous solution (or even an organic solution). Thus, the ion exchange sites and the counterions may be solvated, while the free spaces resulting from the crosslinking and aggregation of the polymer chains may fill with solvent. The degree of swelling, expressed as a percentage, is defined by the ratio of the mass of solvent contained within the membrane to the dry mass of this membrane. The degree of swelling is calculated by the following equation:

$$Tg\ (\%) = \frac{m_{wet} - m_{dry}}{m_{dry}} \times 100$$

in which $m_{wet}$ is the mass (in grams) of the membrane after swelling in the solvent and $m_{dry}$ is the mass (in grams) of the membrane before swelling in the solvent.

Experimentally, the degree of swelling was determined by measuring the water uptake/loss. To do this, the membrane was weighed in the dry state and then after immersion in deionized water for 24 hours and wiping of the faces, and finally after drying the membrane in an oven at 100° C. for 24 hours to determine the amount of water adsorbed. This measurement may also be performed using a drying balance (Mettler, Sartorius, etc. brand) and by measuring the variations in mass between the membrane in hydrated or dry state.

3) Degradation temperature: this was determined graphically on thermograms of the membranes produced by thermogravimetric analysis (TGA) and differential thermal analysis (DTA). The measurements were performed under nitrogen ($N_2$), with a heating temperature of 10° C./minute using machines sold by the company TA Instruments under the references TGA 2950 High Resolution and SDT 2960 Simultaneous.

4) Conductivity: this was determined by impedance spectroscopy. This is a generalization of Ohm's law by measuring the complex impedance Z as a function of the frequency (ω), of a material subjected to a sinusoidal disturbance (input voltage), which gives access to its electrical resistance R according to the following equation:

$$Z(\omega) = \frac{U(\omega)}{I(\omega)}$$
$$= |Z|\exp^{(-j\Phi)}$$
$$= Z'(\omega) + jZ''(\omega)$$
$$= \text{Re}(Z) + \text{Im}(Z)$$

The measurements were taken at a temperature of 25° C. and at 100% relative humidity (RH), with impedance-meters of Solartron® 1260 (analyzer) and 1255 (interface) type using the software packages Zplot® and Zview®. The scanned frequency range is variable, and generally between 0.1 Hz and 10 MHz. The amplitude of the sinusoidal voltage signal was varied between 1 and 1000 mV, the linearity domain commonly accepted for ion conductors. To study the electrochemical properties of the electrolyte, two phases of liquid mercury with direct contact, contained in a two-compartment Teflon cell between which compartments the membrane was held, were used as electrodes. Platinum wires dipping into the mercury were connected to the measuring machines. The mercury was renewed for each measurement, and made it possible especially to obtain very good contacts and to optimize the interface between the two electrodes and the membrane studied.

Graphic representations corresponding to Nyquist diagrams (impedance representation in an orthonormalized basis) were obtained. These impedance diagrams (not shown) describe, in the frequency range studied, the change of the opposite of the imaginary part of the impedance as a function of the value of the real part. The real part Z' of the impedance (on the x-axis) and the opposite of the imaginary part −Z" (on the y-axis) were expressed in ohms ($\Omega$). Thus, the value of the overall intrinsic resistance of the sample R ($\Omega$) was determined graphically, which corresponds to extrapolation or the intersection of the curve with the x-axis. By correlating this value with the geometrical factors of the material, namely the thickness (e) and the exposed surface area (S), the total conductivity expressed in $S \cdot cm^{-1}$ could be calculated according to the following equation:

$$\sigma(S \cdot cm^{-1}) = \frac{e(cm)}{R(\Omega) \times S(cm^2)}$$

The characterizations and experimental measurements on membranes A to G in accordance with the invention and on the commercial membrane of Nafion® 117 type were performed under the same conditions, with the same machines and operating protocols (including the hydration, ion exchange in the presence of acid, and rinsing steps). The results obtained are given in Table 2 below:

The results presented in Table 2 above also show that membrane D containing only 40% by weight of compound (1) has, for a degree of swelling 1.75 times greater, an equivalent degradation temperature and ion exchange capacity, and higher conductivity (×1.45) than that of the reference membrane of Nafion® 117 type. Membranes F and G having a higher composition of compound (1), of 58% and 78% by weight, respectively, show slight differences in terms of swelling and of heat stability, but, on the other hand, have much higher ion exchange capacities and, most interestingly of all, conductivities 4 to 8 times greater than that of the reference membrane of Nafion® 117 type.

Structural analyses by X-ray diffraction of membranes A, D and H thus obtained were performed using a diffractometer sold by the company Philips, PanAnalytical X'pert Pro I model, (measurements in Bragg-Brentano mode, graphite secondary monochromator, X'celerator detector, Cu radiation). These analyses demonstrate the high organization of the hybrid membranes.

Figure 5:
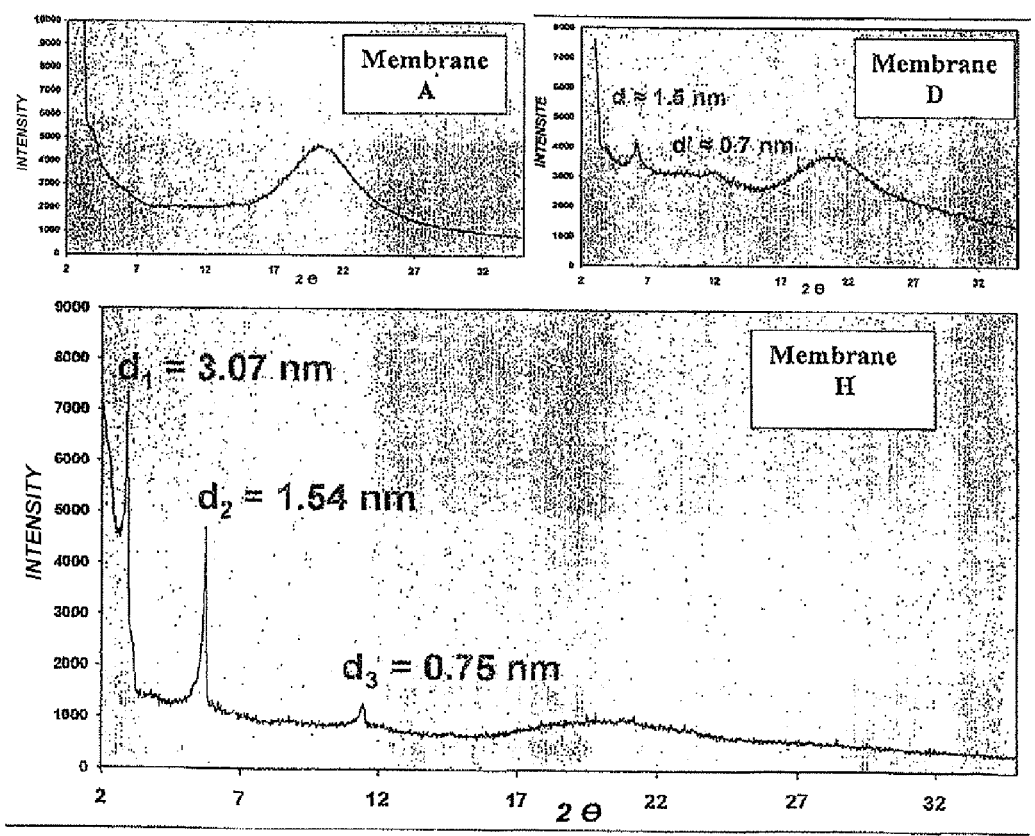
FIG. 5 shows the X-ray diffractograms of hybrid membranes obtained with compound (1), in the presence or absence of a plasticizing precursor (compound 3) compared with a membrane (not forming part of the invention) obtained not using any precursor (1) but just the plasticizing precursor (3): Membrane A obtained with compound (3) alone, Membrane D: obtained with 40% by weight of compound (1) and 60% by weight of compound (3) and Membrane H: obtained using only the precursor (1) without any plasticizing precursor. In this figure, the intensity (in arbitrary units) is a function of the diffraction angle (2θ)

The attached FIG. 5 shows the diffractograms of membranes A, D and H on which the intensity in arbitrary units is expressed as a function of the diffraction angle: $2\theta$.

Figure 6:
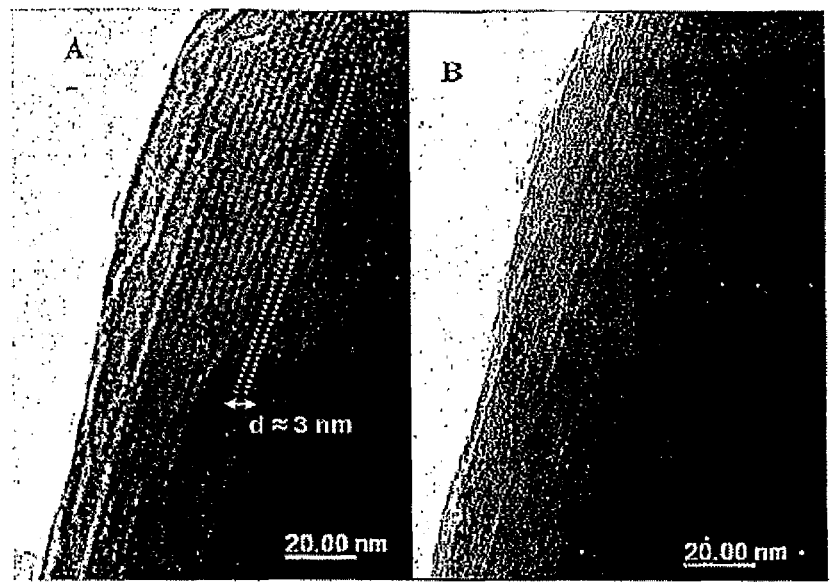
FIG. 6 is a transmission electron microscopy photograph of a membrane formed from a hybrid material based on 100% of precursor (1) polymerized via sol-gel (membrane H of Table 2 of Example 2 below) at a magnification of ×120 000 (FIG. 6A: image at sub-critical focusing, FIG. 6B: image at critical focusing)

It is first noted that in the absence of compound (1) in accordance with the invention (membrane A not forming part of the invention), the material obtained does not have any diffraction peak and is thus amorphous. It is also noted that when the mass content of compound (1) is increased, diffraction peaks emerge in the diffractogram (membranes D and H): this is reflected by very strong discrete peaks, the main one of which (001 type plane) is at small angles and corresponds to an interplane distance centered at 3 nm. The other two peaks, which are weaker, are harmonic peaks in direct relationship with the first, and correspond to the plane of type 002 and of type 004, which demonstrates the presence of a lamellar network organizing into molecular channels with an average width of 3 nm. In this regard, the attached FIG. 6 is a transmission electron microscopy photograph of membrane H at a magnification of ×120 000 (FIG. 6A: image at sub-critical focusing, FIG. 6B: image at critical focusing). This figure demonstrates the structuring in parallel nanometric channels (3 nm) within membrane H.

TABLE 2

| Membrane | Thickness ($\mu$m) | $C_1$ (weight %) | $r_1$ (%) | IEC (meq./g) | Degree of swelling (%) | Hydration number $\lambda$ | Degradation temperature (°C.) | Conductivity $\sigma$ (mS · cm$^{-1}$) |
|---|---|---|---|---|---|---|---|---|
| A (*) | 255 | 0 | 0 | 0 | 6 | 0 | 373 | 0.002 |
| B | 212 | 20 | 47.4 | 0.44 | 18 | 22 | 392 | 4.7 |
| C | 239 | 30 | 60.8 | 0.74 | 33 | 24 | 386 | 15.7 |
| D | 187 | 40 | 64.3 | 0.88 | 44 | 28 | 388 | 32 |
| E | 115 | 48 | 70.6 | 0.97 | 52 | 29 | 334 | 48.4 |
| F | 211 | 58 | 78.3 | 1.26 | 61 | 27 | 356 | 98.5 |
| G | 164 | 78 | 84.2 | 1.46 | 68 | 26 | 376 | 160.2 |
| H | — | 100 | 100 | — | — | — | — | — |
| Nafion ® 117 | 175 | — | — | 0.85 | 25 | 16 | 395 | 22.4 |

(*) Membrane not forming part of the invention

The values $C_1$, $r_1$ and $\lambda$ of Table 2 represent:
$C_1$ is the concentration of compound (1), and is calculated by means of the relationship: $C_2$ (weight %)=100−$C_1$,
$r_1$ is the mole ratio of compound (1), and
$\lambda$ is the hydration number: $\lambda=(n_{H2O}/n_{SO3H})$.

The reference membrane A obtained from compound (3) has a zero ion exchange capacity (IEC), and very poor proton conductivity, which may be attributed to the inorganic silica network and to the absence of functional groups.

Thus, the high crystallinity of the starting compound (1) is transferred into the hybrid network with the formation of highly structured materials. The polymerized and fixed precursors (1) are found in the hybrid network (formation of the inorganic backbone/matrix via bonds of Si—O—Si type), the sulfonic functions of which are oriented toward the interior of the channel. Pairing of the close neighbors generates a fully condensed final architecture in which the nanometric and parallel channels make it possible to define a preferential space for transporting ionic species and particularly for conducting protons ($H^+$).

Figure 7:
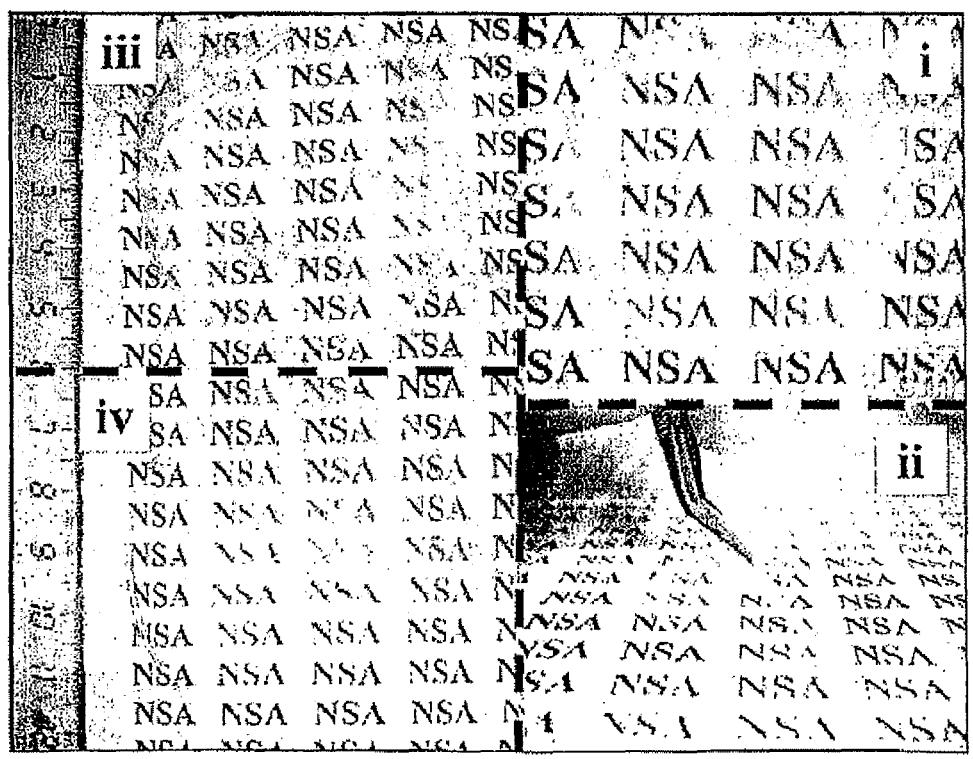
FIG. 7 shows photographs of hybrid membranes in accordance with the invention, these membranes having been placed on a printed support; in this figure, photographs (i) and (ii) are those of membrane D of Table 2 of Example 2 described below, composed of 40% by weight of precursor (1), photograph (iii) is that of membrane F of Table 2 of Example 2 described below, composed of 58% by weight precursor (1) and photograph (iv) is that of membrane E of Table 2 of Example 2 described below, composed of 48% by weight of compound (1)

The attached FIG. 7 shows photographs of the hybrid membranes D (FIGS. 7i and 7ii), F (FIG. 7iii) and E (FIG. 7iv), these membranes having been placed on a printed support.

Figure 8:
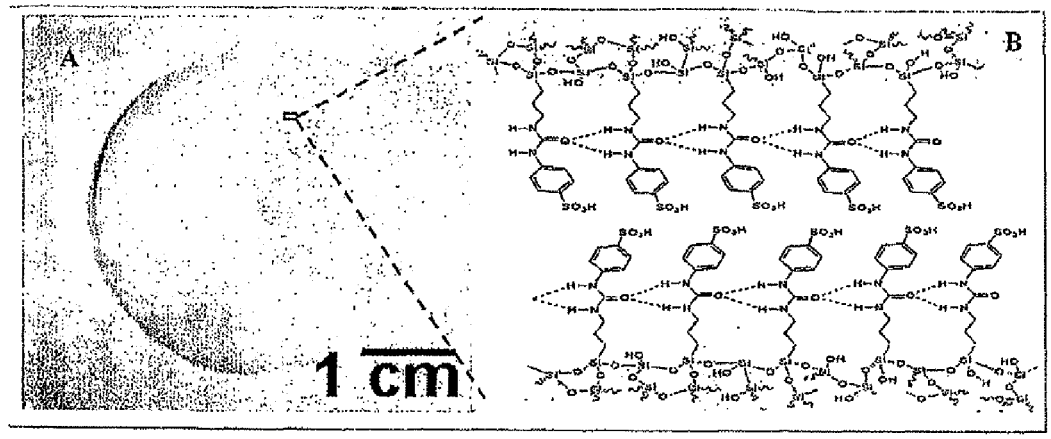
FIG. 8 is a photograph of membrane H in accordance with the present invention and composed solely of the hybrid material based on the precursor (1) polymerized via sol-gel (FIG. 8A), and also a schematic representation (FIG. 8B) of a proton channel existing within the lamellar structure of such a hybrid membrane.

FIG. 8 is a photograph of membrane H composed solely of the precursor (1) (FIG. 8A) and also a schematic representation (FIG. 8B) of a proton channel existing within the hybrid matrix of such a material which thus reveals a lamellar structure. For this type of structure, composed of successive planes, it may be defined that the inorganic backbone $(Si-O-Si)_n$ forms the walls/partitions of the conduction channels, whereas the interior of the channels is formed by the grouping of the organic parts and more particularly of the sulfonate functions.

Figure 9:
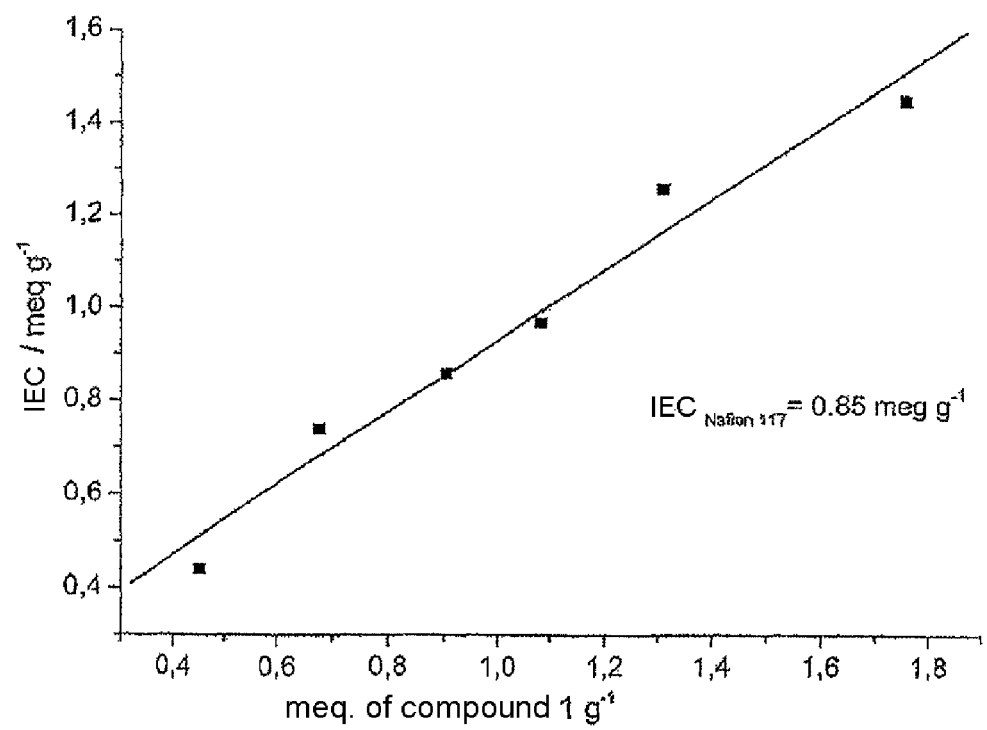
FIG. 9 represents the ion-exchange capacity (IEC) of membranes A to H at room temperature as a function of the meq. of compound (3) per gram of membrane.

It is seen in FIG. 9 that the Ion Exchange Capacity (IEC) of the measured membranes B to H are very close to the theoretical values calculated from the molar amounts (in meq.g$^{-1}$) of compound (3), which means that the protons of the sulfonate groups are accessible during the titration and participate in the proton conduction process.

Figure 10:
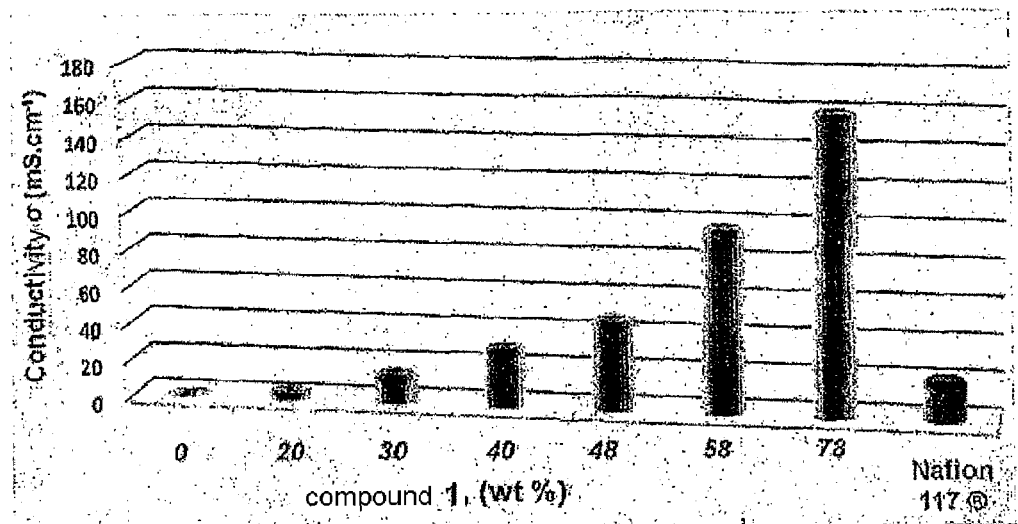
FIG. 10 represents the proton conductivity at 25° C. and 100% relative humidity of membranes A to H and of the reference membrane of Nafion® 117 type.

FIG. 10 shows that membrane D containing only 40% by weight of compound (1) achieves higher proton conductivity than that of Nafion® 117 for an equal Ion Exchange Capacity (IEC) and a higher degree of swelling. The superiority of the proton conductivities measured for membranes D to H may be attributed to the increase in the number of nanodomains having a high concentration of sulfonate groups (*J. Power Sources* 2006, 154, 115-123).

Figure 11:
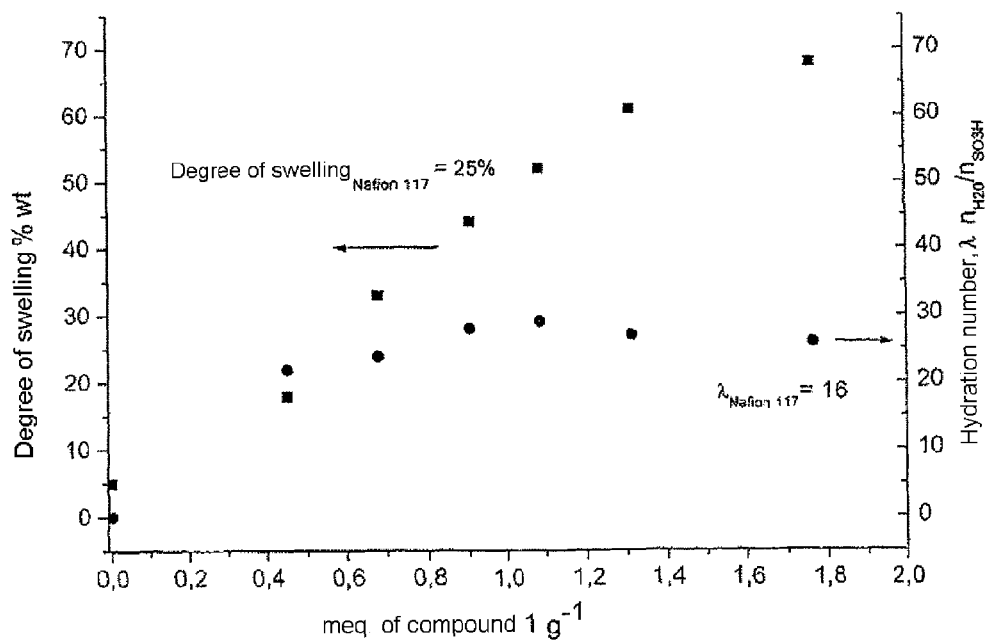
FIG. 11 represents the degree of swelling and the hydration number of membranes A to H at room temperature as a function of the meq. of compound (3) per gram of membrane.

FIG. 11 shows a linear increase in the degree of swelling of membranes B to H, while the hydration number λ remains constant.

Figure 12:
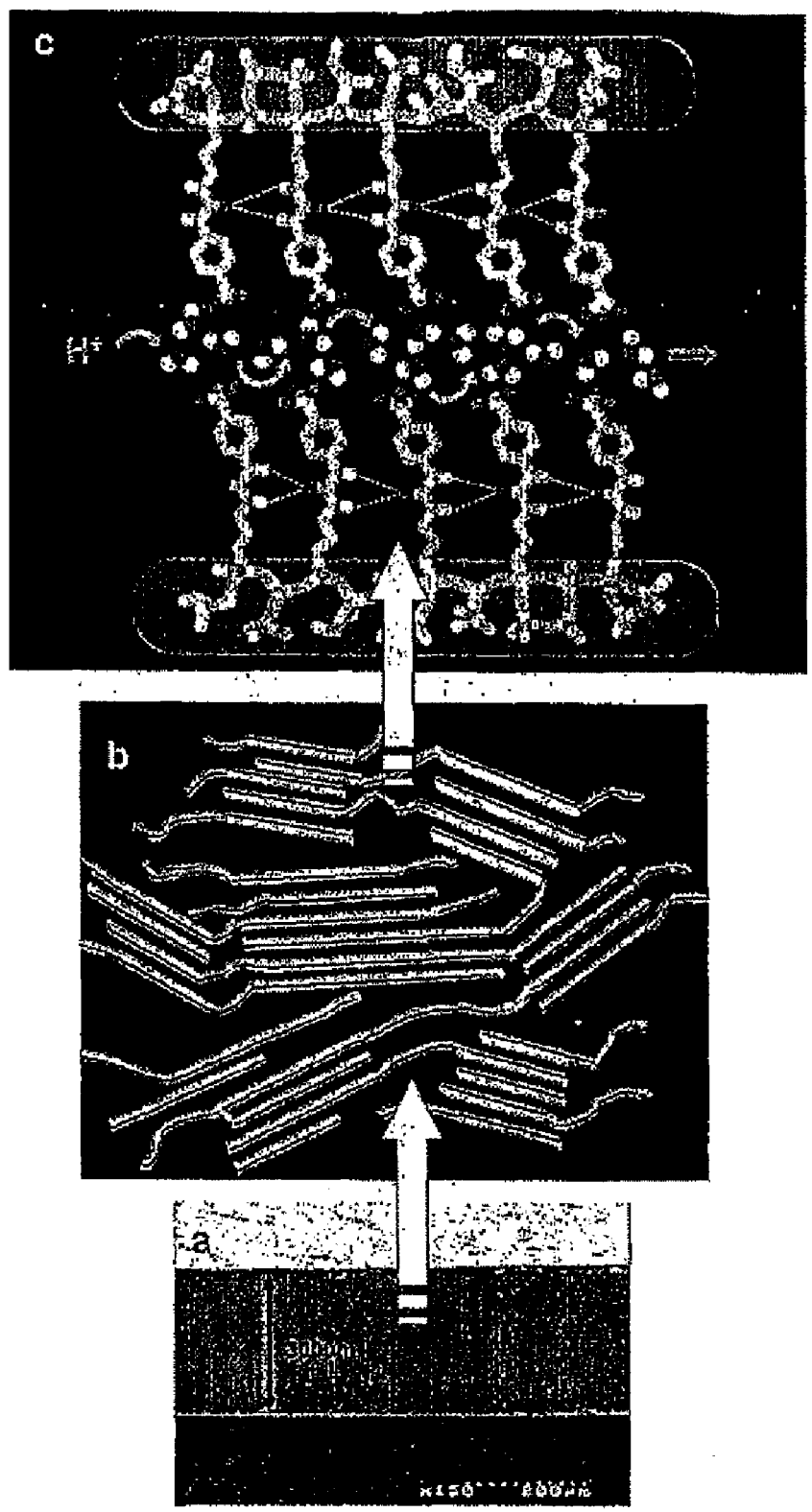
FIG. 12 schematically represents the mechanism of formation of the hybrid membranes of the invention.

These data are confirmed by FIG. 12, which shows the formation of the channels. While the degree of swelling increases constantly with the Ion Exchange Capacity (IEC), a more pronounced increase in conductivity with the Ion Exchange Capacity (IEC) is recorded for membranes E to H relative to membranes B to D. For membranes E to H, the high concentration of compound (1) extends the density and the orientation of the sulfonate groups, thus leading to a highly concentrated conductive network of high proton conductivity. The proton conductivity of the PEM membranes (Polymer Electrolyte Membrane) is a key parameter that depends greatly on the Ion Exchange Capacity (IEC) and on the temperature, and the activation energy Ea of which gives an insight into the transportation mechanism. One of the drawbacks of Nafion® 117 is that it is difficult to apply to DMFC (Direct Methanol Fuel Cell) membranes, since the permeability of methanol is directly linked to the structure of Nafion® 117, the ion-conducting domains of which contribute toward rapid diffusion of the methanol (*J. Power Sources*, 2008, 175, 256-260).

Membrane I has a conductivity $\delta=25$ mS·cm$^{-1}$ that is almost equal to the conductivity of Nafion® 117 ($\sigma=22.4$ mS·cm$^{-1}$ determined experimentally). The methanol permeability of membrane I ($P_M=4.1\times10^{-7}$ cm$^2$/s at 25° C.) is reduced by 23% relative to the methanol permeability of Nafion® 117 ($P_M=18.1\times10^{-7}$ cm$^2$/s at 25° C.). Ideally, a DMFC (Direct Methanol Fuel Cell) membrane should have high proton conductivity and low methanol permeability, the selectivity of the membrane for proton transport in methanol being equal to $\beta=\sigma/P_m$. For membrane I: $\beta=61\times10^{-6}$ mS·s·cm$^{-1}$, this selectivity being approximately ten times greater than that of Nafion® 117. This increase is due to the decrease in methanol permeability, since membrane I and Nafion® 117 have the same proton conductivity.

The activation energy Ea is determined according to the Arrhenius law:

$$\sigma=\sigma_0 exp(-Ea/RT)$$

where:

Ea is the Arrhenius activation energy,

T is the temperature, and

R is the perfect gas constant (usual value: R=8.314 J·mol$^{-1}$·K$^{-1}$).

As shown by FIG. 13, the values obtained are approximately:

for membrane I: Ea=17.46 kJ·mol$^{-1}$, for Nafion® 117: Ea=13.32 kJ·mol$^{-1}$.

The activation energy value Ea obtained for membrane I relative to that of Nafion® 117 suggests the presence of a more compact superstructure for membrane I in which the water molecules (and also the methanol molecules) are less mobile (when compared with the structure of Nafion® 117).

The invention claimed is:

1. A compound of formula (I) below:

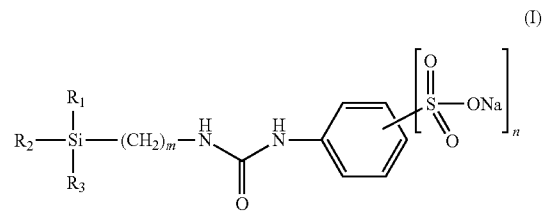

in which:

$R_1$ and $R_3$ are identical and represent a methyloxy or ethyloxy radical;

$R_2$ represents a methyl, ethyl, methyloxy, ethyloxy or phenyl radical;

m is an integer ranging from 2 to 6 inclusive;

n is an integer equal to 1 or 2.

2. The compound as claimed in claim 1, characterized in that $R_1$ and $R_3$ represent an ethyloxy radical.

3. The compound as claimed in claim 1, characterized in that $R_2$ represents an ethyloxy radical.

4. The compound as claimed in claim 1, characterized in that m=3.

5. The compound as claimed in claim 1, characterized in that n=1 and the sodium sulfonate group occupies the para position of the phenyl ring relative to the carbon atom linked to the nitrogen atom of the urea group.

6. The compound as claimed in claim 1, characterized in that n=2 and the two sulfonate groups are either each in the meta position relative to the carbon atom linked to the nitrogen atom of the urea group, or, respectively, in the para and meta position relative to the carbon atom linked to the nitrogen atom of the urea group.

7. The compound as claimed in claim 1, characterized in that it is chosen from those in which n=1.

8. The compound of formula (I) as claimed in claim 1, characterized in that it is 3-(triethoxysilyl)propyl)-3-(4-sodium sulfonate)phenyl)urea of the following formula:

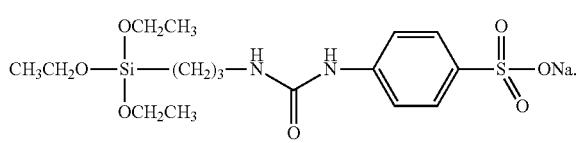

9. A process for synthesizing the compounds of formula (I) comprising the following steps:
1) totally dehydrating an aminobenzene sulfonate of formula (II) below:

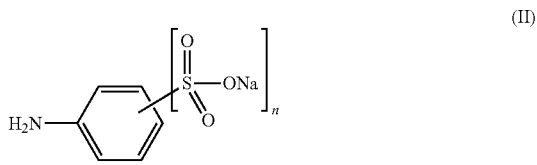

in which n is an integer equal to 1 or 2, to obtain an anhydrous aminobenzene sulfonate of formula (II),
2) dissolving the anhydrous aminobenzene sulfonate of formula (II) obtained above in the preceding step in an anhydrous organic solvent chosen from methanol, dimethylformamide and N,N-dimethylacetamide and mixtures thereof;
3) placing said solution under vacuum and under an inert atmosphere;
4) adding to said solution, in excess and at room temperature, an anhydrous isocyanate compound of formula (III) below:

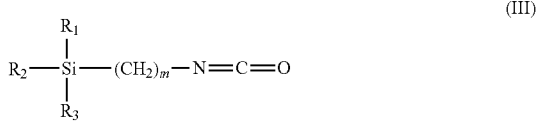

in which:
$R_1$ and $R_3$ are identical and represent a methyloxy or ethyloxy radical;
$R_2$ represents a methyl, ethyl, methyloxy, ethyloxy or phenyl radical;
m is an integer ranging from 2 to 6 inclusive;

5) precipitating the expected compound of formula (I) in an aprotic solvent; and
6) washing said compound of formula (I) in an aprotic solvent.

10. The process as claimed in claim 9, characterized in that the solvent of step 2) is anhydrous methanol.

11. The process as claimed in claim 9, characterized in that, during step 4), the isocyanate compound of formula (III) is used in an excess representing from 1.2 to 1.3 equivalents relative to the amount of aminobenzene sulfonate of formula (II) used.

12. The process as claimed in claim 9, characterized in that, after step 4), the solution containing the aminobenzene sulfonate of formula (II) and the isocyanate compound of formula (III) is brought to a temperature of between 60 and 80° C. inclusive, for a time ranging from 3 to 12 hours.

13. The process as claimed in claim 9, characterized in that the aprotic solvent used in steps 5) and 6) is chosen from acetonitrile, ether, acetone, and mixtures thereof.

14. A proton-conducting electrolyte polymer membrane comprising at least one compound of formula (I) as defined in claim 1.

15. The proton-conducting electrolyte polymer membrane as claimed in claim 14, characterized in that the compound of formula (I) is 3-(triethoxysilyl)propyl)-3-(4-sodium sulfonate)phenyl)urea.

16. A functional hybrid filler in a host structure after in situ sol-gel polymerization, said functional hybrid filler comprising at least one compound of formula (I) as defined in claim 1.

17. Functional hybrid nanoparticles comprising at least one compound of formula (I) as claimed in claim 1.

18. A thinning agent comprising at least one compound of formula (I) as claimed in claim 1.

19. A surface coating comprising at least one compound of formula (I) as claimed in claim 1.

20. A hygroscopic agent comprising at least one compound of formula (I) as claimed in claim 1.

21. A binder comprising at least one compound of formula (I) as claimed in claim 1.

22. A structuring agent comprising at least one compound of formula (I) as claimed in claim 1.

* * * * *

UNITED STATES PATENT AND TRADEMARK OFFICE
CERTIFICATE OF CORRECTION

PATENT NO. : 8,357,817 B2  Page 1 of 1
APPLICATION NO. : 12/933593
DATED : January 22, 2013
INVENTOR(S) : Barboiu et al.

It is certified that error appears in the above-identified patent and that said Letters Patent is hereby corrected as shown below:

In the claims:

*In the claims section, Claim 7, Column 18, Line 64, please delete the text as indicated below:*

7. The compound as claimed in claim 1 ~~any one of the preceding claims~~, characterized in that ~~it is chosen from those in which~~ n = 1.

*In the claims section, Claim 9(2) Column 19, Line 25, please delete the text and add punctuation as indicated below:*

9.
    2) dissolving the anhydrous aminobenzene sulfonate of formula (II) obtained above in the preceding step in an anhydrous organic solvent chosen from methanol, dimethylformamide, ~~and~~ N,N-dimethylacetamide and mixtures thereof;

Signed and Sealed this
Twentieth Day of August, 2013

Teresa Stanek Rea
*Acting Director of the United States Patent and Trademark Office*